United States Patent
Chiang et al.

(10) Patent No.: US 8,563,589 B2
(45) Date of Patent: Oct. 22, 2013

(54) METHODS OF TREATING NEUROPATHIC PAIN WITH BENZIMIDAZOLE DERIVATIVE AGONISTS OF PPARGAMMA

(76) Inventors: Lillian W. Chiang, Princeton, NJ (US); Tage Honore, Princeton, NJ (US)

( * ) Notice: Subject to any disclaimer, the term of this patent is extended or adjusted under 35 U.S.C. 154(b) by 12 days.

(21) Appl. No.: 12/845,868

(22) Filed: Jul. 29, 2010

(65) Prior Publication Data

US 2011/0028527 A1 Feb. 3, 2011

Related U.S. Application Data

(60) Provisional application No. 61/229,912, filed on Jul. 30, 2009.

(51) Int. Cl.
  *A01N 43/52* (2006.01)
  *A61K 31/415* (2006.01)
  *C07D 235/00* (2006.01)
  *C07D 401/00* (2006.01)

(52) U.S. Cl.
  USPC ............... 514/394; 548/309.7; 546/273.4

(58) Field of Classification Search
  USPC ............... 514/394; 548/309.7; 546/273.4
  See application file for complete search history.

(56) References Cited

FOREIGN PATENT DOCUMENTS

EP 882718 A1 * 12/1998
WO WO 0213812 A1 * 2/2002

OTHER PUBLICATIONS

Medscape Reference; Lin et al. Diabetic Neuropathy, Medscape reference, Published online Dec. 2008, pp. 1-11.*
Fujimara et al. J. Pharmacol. Sci., 2005, vol. 99, pp. 342-352.*

* cited by examiner

*Primary Examiner* — Samira Jean-Louis
(74) *Attorney, Agent, or Firm* — F. Aaron Dubberley

(57) ABSTRACT

Embodiments of the invention relate to the treatment of neuropathic pain in mammals. Embodiments of the invention include methods for treating neuropathic pain with benzimidazole derivatives with PPARgamma agonist activity, as well as methods for preparing medicaments used in such treatments of mammalian pain.

3 Claims, 4 Drawing Sheets

METHODS OF TREATING NEUROPATHIC PAIN WITH BENZIMIDAZOLE DERIVATIVE AGONISTS OF PPARGAMMA

FIELD

Embodiments of the invention relate to the treatment of pain, including neuropathic pain, in mammals.

BACKGROUND

Neuropathic Pain

Pain is the most common symptom for which patients seek medical help, and can be classified as either acute or chronic. Acute pain is precipitated by immediate tissue injury (e.g., a burn or a cut), and is usually self-limited. This form of pain is a natural defense mechanism in response to immediate tissue injury, preventing further use of the injured body part, and withdrawal from the painful stimulus. It is amenable to traditional pain therapeutics, including non-steroidal anti-inflammatory drugs (NSAIDs) and opioids. In contrast, chronic pain is present for an extended period, e.g., for 3 or more months, persisting after an injury has resolved, and can lead to significant changes in a patient's life (e.g., functional ability and quality of life) (Foley, Pain, In: Cecil Textbook of Medicine, pp. 100-107, Bennett and Plum eds., 20th ed., 1996).

Chronic debilitating pain represents a significant medical dilemma. Pain can be classified as either "nociceptive" or "neuropathic". "Nociceptive pain" results from activation of pain sensitive nerve fibers, either somatic or visceral. Nociceptive pain is generally a response to direct tissue damage. The term "neuropathic pain" refers to pain that is due to injury or disease of the central or peripheral nervous system. In contrast to the immediate pain caused by tissue injury, neuropathic pain can develop days or months after a traumatic injury. Furthermore, while pain caused by tissue injury is usually limited in duration to the period of tissue repair, neuropathic pain frequently is long lasting or chronic. Moreover, neuropathic pain can occur spontaneously or as a result of stimulation that normally is not painful. Neuropathic pain is common in the following conditions: postherpetic neuralgia, trigeminal neuralgia, AIDS-related neuropathy, causalgia, diabetic neuropathy, chronic low back pain, back and neck pain with neuropathic involvement, phantom limb pain, atypical facial pain and cancer neuropathy (Berger et al., 2004, J. Pain 5:143-149).

Unfortunately, neuropathic pain is often resistant to available drug therapies; a hallmark of neuropathic pain is its intractability. Typical non-steroidal anti-inflammatory drugs (NSAIDs) such as aspirin, indomethecin, and ibuprofen do not relieve neuropathic pain. The neuropathic pain observed in animal models predictive of human clinical outcome does not respond to NSAIDs. Treatments for neuropathic pain include opioids, anti-epileptics, NMDA antagonists, topical Lidocaine, topical Capsaicin and tricyclic anti-depressants. Current therapies have limited efficacy and may have serious side effects such as abuse potential, cognitive changes, sedation, and nausea. Many patients suffering from neuropathic pain have limited tolerance of such side effects. Accordingly, there is a need for additional neuropathic pain therapies.

PPAR Gamma Signaling Pathway and Modulators Thereof

The peroxisome proliferator-activated receptors (PPARs: α β/δ and γ) are a subfamily of ligand-inducible nuclear hormone transcription factors with roles in a range of physiological processes and disease states. PPARγ is widely expressed, particularly in tissues important for insulin action such as adipose tissue, skeletal muscle and liver. In the treatment of diabetes, activation of PPARγ improves glycemic control by improving insulin sensitivity, via activation of genes involved in the control of glucose production, transport and utilization.

PPARα is localized in tissues of the heart, liver and muscle, where it plays an important role in lipid metabolism by controlling genes relating to cellular free fatty acid metabolism and cholesterol trafficking PPARα activation decreases serum triglycerides (TGs) and increases levels of serum high-density lipoprotein (HDL)-cholesterol. Hypertriglyceridemia and low serum HDL-cholesterol are characteristic of both diabetic dyslipidemia and insulin resistance syndrome.

PPARγ has been identified as a potential target for neuropathic pain therapeutics, but the mechanism of neuropathic pain treatment through modulation of PPARγ has not been elucidated and is not understood. The Inventor's previously published PCT Patent Application WO 2008/063842 teaches PPARγ agonists as therapeutic agents for treating neuropathic pain. Other publications suggest antagonism of PPARγ for neuropathic pain therapy. In Published PCT Patent Application WO2006085686, *Remedy for Neurogenic Pain*, Tanabe & Tsutomu, Tokyo Medical & Dental University state: " . . . it is intended to provide a remedy for neurogenic pain which contains, as the active ingredient, a PPARgamma antagonist (such as 2-chloro-5-nitro-N-phenylbenzamide) . . . a medicinal composition for treating neurogenic pain which contains, as the active ingredient, a PPAR antagonist . . . " Tanabe and Tsutomu demonstrate that GW9662, a PPARγ antagonist demonstrates activity in a neurogenic pain model. Accordingly it is not clear whether agonism or antagonism of PPARγ results in therapeutic effects on neuropathic pain.

Even among the PPARγ agonists specifically taught by Published PCT Patent Application WO 2008/063842 (Tesaglitazar, Muraglitazar, Peliglitazar, Farglitazar, Reglitazar, Naveglitazar, Oxeglitazar, Edaglitazone, Imiglitazar and Sipoglitazar), further animal model testing has revealed a diversity of results. For instance, neither of Muraglitazar or Tesaglitazar showed any statistically significant difference from a vehicle control in the Bennett neuropathic pain animal model described below. See FIG. 1 for results. Therefore, it is not predictable whether any particular agonist or antagonist will or will not therapeutically reduce neuropathic pain.

Published PCT Applications WO 97/24334 and WO 00/29383 to Noritsugu Yamasaki et al., and related U.S. Pat. Nos. 6,166,219, 6,352,985, 6,703,410 and EP Patent 0882718 B1 teach benzimidazole derivatives having hypoglycemic or PPARγ agonist activity. Each of these patents and patent applications is incorporated herein by reference. Yamasaki et al. teach PPARγ agonist benzimidazole derivatives of Formula I:

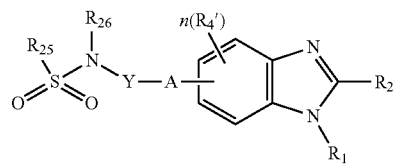

wherein $R_1$ represents a hydrogen atom, an arylsulfonyl group, or a lower alkyl group; said lower alkyl group may be substituted by an aryl group or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyloxy group, an arylsulfonyl-lower alkyl group, an aryl-lower alkyl group, a haloaryl-lower alkyloxy group, an arylsulfonylamino group, an arylcarbonylamino group, an arylcarbonyl group, an arylalkenyl group, a cyanoaryl group, and a heterocyclic group, or by a heterocyclic group;

$R_2$ represents a hydrogen atom, a lower cycloalkyl group, a hydroxyl group, a hydroxy-lower alkyl group, a lower alkoxy group, a mercapto group, a lower alkylthio group, an amino group, a lower alkylamino group, a carboxyl group, an aryl group, or a lower alkyl group; said lower alkyl group may be substituted by a halogen atom, a lower alkoxy group, a cyano group, a halocarbonyl group, an aryl group, or a heterocyclic group;

$R_{25}$ represents an alkyl group having up to 8 carbon atoms, a lower cycloalkyl group, a halo-lower alkyl group, a tri-lower alkylsilyl-lower alkyl group, a lower alkoxy-lower alkyl group, a lower alkylthio-lower alkyl group, an aryl group, a heterocyclic group, an aryl-lower alkyl group, or a hydroxy-lower alkyl group; said aryl group may be substituted by a halogen atom, a lower alkyl group, a halo-lower alkyl group, a lower alkoxy group, or a nitro group;

$R_{26}$ represents a hydrogen atom or a lower alkyl group; provided that, when $R_{25}$ and $R_{26}$ are both lower alkyl groups, they may be bonded together to form a ring;

Y represents a carbonyl group or a lower alkylene group;

A represents a single bond, or a lower alkylene or alkenylene group;

$R_4'$ represents a hydrocarbon group or a halogenated hydrocarbon group; and n means an integer from 0 to 3;

wherein the arylsulfonyl group is selected from a benzenesulfonyl group, a toluenesulfonyl group, and a naphthalenesulfonyl group;

the term "lower" indicates that the group has from 1 to 6 carbon atoms, unless otherwise specifically indicated;

the aryl group is selected from a phenyl group and a naphthyl group, which may optionally be substituted by one or more substituents selected from a halogen atom, a lower alkyl group, a cyano group, a nitro group and a trifluoromethyl group;

the halo-lower alkyl group is a linear or branched alkyl group having up to 8 carbon atoms, which is substituted with one or more halogen atoms;

the heterocyclic group is selected from a pyridyl group, a quinolyl group, an isoquiriolyl group, a thiazolyl group, a thiadiazolyl group, a benzofuranyl group, a dibenzofuranyl group, a thianaphthalenyl group, a 1H-1,2,3-triazolyl group, a 1,2,4-triazolyl group, a tetrazolyl group, a furyl group, a thienyl group, a pyrrolyl group, an imidazolyl group, a pyrimidinyl group, an indolyl group, a benzimidazolyl group, which groups may optionally be substituted by one or more substituents of halogen atoms and lower alkyl groups; and the lower cycloalkyl group is a cycloalkyl group having from 3 to 7 carbon atoms or a pharmaceutically acceptable salt thereof.

Yamasaki et al. further teach PPARγ agonist benzimidazole derivatives of Formula II:

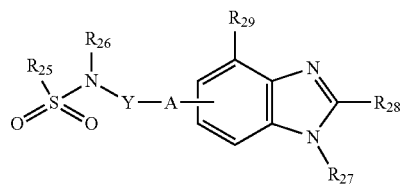

wherein:

$R_{27}$ represents a hydrogen atom, a lower alkyl group, an arylsulfonyl group or an aryl-lower alkyl group; wherein the aromatic ring moiety in said aryl-lower alkyl group may be substituted by one or two substituents selected from a halogen atom, a lower alkyl group, a halo-lower alkyl group, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an arylcarbonyl group, an arylcarbonylamino group, and an aryl-lower alkyloxy group substituted by one or two halogen atoms;

$R_{28}$ represents a hydrogen atom, a lower alkyl group, a halo-lower alkyl group, a lower alkoxy-lower alkyl group, a lower cycloalkyl group, an aryl group, an aryl-lower alkyl group, a lower alkylamino group, a lower alkoxy group, a lower alkylthio group, a hydroxyl group, a mercapto group, an amino group, or a carboxyl group;

$R_{25}$ represents an alkyl group having up to 8 carbon atoms, a halo-lower alkyl group, a tri-lower alkylsilyl-lower alkyl group, a lower alkoxy-lower alkyl group, a lower alkylthio-lower alkyl group, an aryl group, a heterocyclic group, an aryl-lower alkyl group, or a hydroxy-lower alkyl group; said aryl group may be substituted by a halogen atom, a lower alkyl group, a halo-lower alkyl group, a lower alkoxy group, or a nitro group;

$R_{26}$ represents a hydrogen atom or a lower alkyl group; provided that, when $R_{25}$ and $R_{26}$ are both lower alkyl groups, they may be bonded together to form a ring;

Y represents a carbonyl group or a lower alkylene group;

A represents a single bond, or a lower alkylene or alkenylene group; and $R_{29}$ represents a hydrogen atom or a lower alkyl group or a pharmaceutically acceptable salt thereof.

Yamasaki et al. further teach PPARγ agonist benzimidazole derivatives of Formula II, wherein all groups are as given above, except:

$R_{27}$ represents an aryl lower alkyl group whose aryl moiety may be substituted by one or two substituents selected from the group consisting of a halogen atom, a lower alkyl group, a halo-lower alkyl group, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an arylcarbonyl group, an arylcarbonylamino group, and an aryl-lower alkyloxy group substituted by one or two halogen atoms;

Y represents a carbonyl group; and

A represents a single bond.

Yamasaki et al. further teach PPARγ agonist benzimidazole derivatives of Formula II, wherein all groups are as given above, except:

$R_{27}$ represents an aryl lower alkyl group whose aryl moiety may be substituted by one or two substituents selected from a halogen atom or an aryl group;

$R_{28}$ represents a lower alkyl group or a lower cycloalkyl group;

$R_{25}$ represents an alkyl group having up to 8 carbon atoms or an aryl group;

Y represents a carbonyl group; and

A represents a single bond.

All chemical groups recited herein are defined according to the disclosure of Yamasaki et al. in EP 0882718 B1.

Particular PPARγ agonist benzimidazole derivatives taught by Yamasaki et al. include 3-(2,4-dichlorobenzyl)-2-methyl-N-(pentylsulfonyl)-3H-benzimidazole-5-carboxamide, 6-benzenesulfonylcarbamoyl-1-(2-chlorobenzyl)-2-methylbenzimidazole, 1-(biphenyl-4-ylmethyl)-6-(1-butanesulfonylcarbamoyl)-2-methylbenzimidazole, 1-(biphenyl-4-ylmethyl)-6-(1-butanesulfonylcarbamoyl)-2-ethylbenzimidazole, 6-benzenesulfonylcarbamoyl-2-cyclopropyl-1-(2-fluorobenzyl)-benzimidazole, 6-benzenesulfonylcarbamoyl-1-(2,4-dichlorobenzyl)-2-methylbenzimidazole, 6-benzenesulfonylcarbamoyl-1-(2,4-difluorobenzyl)-2-methylbenzimidazole, 6-(1-butanesulfonylcarbamoyl)-1-[(3-fluorobiphenyl-4-yl)methyl]-2-methylbenzimidazole, 1-(2,4-dichlorobenzyl)-2-methyl-6-(1-pentanesulfonylcarbamoyl)benzimidazole, 1-(4-biphenylmethyl)-2-ethyl-6-(1-pentanesulfonylcarbamoyl)benzimidazole, and pharmaceutically acceptable salts thereof.

Yamasaki et al. also teach methods of making the above PPARγ agonist benzimidazole derivatives, formulating them into pharmaceutical compositions and administering them in doses from 0.1 to 100 mg/kg, one to four times a day.

The benzimidazole derivative 3-(2,4-dichlorobenzyl)-2-methyl-N-(pentylsulfonyl)-3H-benzimidazole-5-carboxamide completed a Phase I clinical trial for Astellas Pharma Inc., and was entered into a Phase II clinical trial for type 2 diabetes (see clinicaltrials.gov, trial identifier NCT00036192). "While [3-(2,4-dichlorobenzyl)-2-methyl-N-(pentylsulfonyl)-3H-benzimidazole-5-carboxamide] advanced to Phase II clinical trials, its development was recently discontinued when no advantage [for type 2 diabetes] was demonstrated in clinical trials," Meinke, Peter T., et al., "Nuclear Hormone Receptor Modulators for the Treatment of Diabetes and Dyslipidemia", Annual Reports in Medicinal Chemistry (2006) 141:99-126, p. 109.

SUMMARY

Neuropathic pain in mammals is treated by the administration of a therapeutically effective amount of an agonist of Peroxisome Proliferator-Activated Receptor gamma (PPARγ), wherein the agonist is a compound of Formula I or Formula II.

An embodiment of the invention is a composition for the treatment of neuropathic pain comprising at least one agonist of the PPARγ or a salt, ester, hydrate, solvate, prodrug or polymorph thereof, incorporated in a pharmaceutically acceptable adjuvant, excipient, diluent or carrier composition, wherein the agonist is a compound of Formula I or Formula II.

An embodiment of the invention is a method of treating neuropathic pain in a mammal in need of such treatment, comprising administering a therapeutically effective amount of an agonist of PPARγ or a salt, ester, hydrate, solvate, prodrug or polymorph thereof, wherein the agonist is a compound of Formula I or Formula II.

An embodiment of the invention is a method of treating neuropathic pain in a mammal in need of such treatment comprising administering a therapeutically effective amount of a compound selected from the group consisting of 3-(2,4-dichlorobenzyl)-2-methyl-N-(pentylsulfonyl)-3H-benzimidazole-5-carboxamide, 6-benzenesulfonylcarbamoyl-1-(2-chlorobenzyl)-2-methylbenzimidazole, 1-(biphenyl-4-ylmethyl)-6-(1-butanesulfonylcarbamoyl)-2-methylbenzimidazole, 1-(biphenyl-4-ylmethyl)-6-(1-butanesulfonylcarbamoyl)-2-ethylbenzimidazole, 6-benzenesulfonylcarbamoyl-2-cyclopropyl-1-(2-fluorobenzyl)-benzimidazole, 6-benzenesulfonylcarbamoyl-1-(2,4-dichlorobenzyl)-2-methylbenzimidazole, 6-benzenesulfonylcarbamoyl-1-(2,4-difluorobenzyl)-2-methylbenzimidazole, 6-(1-butanesulfonylcarbamoyl)-1-[(3-fluorobiphenyl-4-yl)methyl]-2-methylbenzimidazole, 1-(2,4-dichlorobenzyl)-2-methyl-6-(1-pentanesulfonylcarbamoyl)benzimidazole, 1-(4-biphenylmethyl)-2-ethyl-6-(1-pentanesulfonylcarbamoyl)benzimidazole and salts, hydrates, solvates, esters, prodrugs, and polymorphs thereof.

Another embodiment of the invention comprises compositions used for treating neuropathic pain comprising at least one compound selected from the group consisting of 3-(2,4-dichlorobenzyl)-2-methyl-N-(pentylsulfonyl)-3H-benzimidazole-5-carboxamide, 6-benzenesulfonylcarbamoyl-1-(2-chlorobenzyl)-2-methylbenzimidazole, 1-(biphenyl-4-ylmethyl)-6-(1-butanesulfonylcarbamoyl)-2-methylbenzimidazole, 1-(biphenyl-4-ylmethyl)-6-(1-butanesulfonylcarbamoyl)-2-ethylbenzimidazole, 6-benzenesulfonylcarbamoyl-2-cyclopropyl-1-(2-fluorobenzyl)-benzimidazole, 6-benzenesulfonylcarbamoyl-1-(2,4-dichlorobenzyl)-2-methylbenzimidazole, 6-benzenesulfonylcarbamoyl-1-(2,4-difluorobenzyl)-2-methylbenzimidazole, 6-(1-butanesulfonylcarbamoyl)-1-[(3-fluorobiphenyl-4-yl)methyl]-2-methylbenzimidazole, 1-(2,4-dichlorobenzyl)-2-methyl-6-(1-pentanesulfonylcarbamoyl)benzimidazole, 1-(4-biphenylmethyl)-2-ethyl-6-(1-pentanesulfonylcarbamoyl)benzimidazole and salts, hydrates, solvates, esters, prodrugs, and polymorphs thereof, incorporated in a pharmaceutically acceptable adjuvant, excipient, diluent, or carrier composition.

To apply the benzimidazole derivatives according to the present invention, they may be formulated into pharmaceutical compositions of ordinary forms, which comprise, as an active ingredient, any of the derivatives along with pharmaceutically acceptable carriers, such as organic or inorganic solid or liquid vehicles, and which are suitable for per oral administration, parenteral administration or external application. The pharmaceutical compositions may be of any solid form of tablets, granules, powders, capsules, etc., or may be of any liquid form of solutions, suspensions, syrups, emulsions, lemonades, etc.

If desired, the pharmaceutical compositions may further contain a pharmaceutical aid, a stabilizer, a wetting agent, and also any ordinary additive of, for example, lactose, citric acid, tartaric acid, stearic acid, magnesium stearate, terra alba, sucrose, corn starch, talc, gelatin, agar, pectin, peanut oil, olive oil, cacao butter, ethylene glycol, etc.

The amount of the above-mentioned derivative of the present invention to be used shall vary, depending on the age and the condition of patients, the type and the condition of diseases or disorders, and the type of the derivative to be used. In general, for peroral administration, the dose of the derivative may be from 0.01 to 1 mg/kg; and for intramuscular injection or intravenous injection, it may be from 1 to 100 µg/kg. Such a unit dose may be applied to a patient once to four times a day.

DETAILED DESCRIPTION

Figure 1:
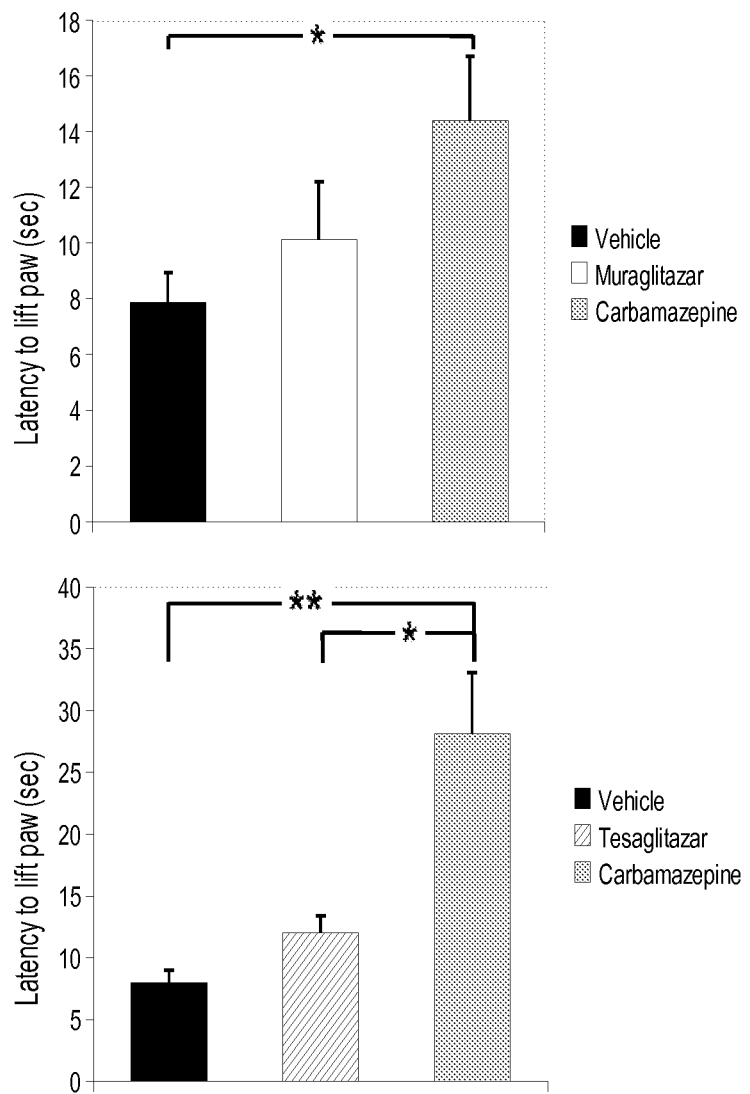
FIG. 1—Efficacy of PPARγ agonists Muraglitizar and Tesaglitizar in Bennett animal model for neuropathic pain. PPAR agonist compounds and positive control carbamazepine were dosed orally at 100 mg/kg, and pain behavior was measured one hour later with the cold allodynia test, as the latency time to removal of the affected paw from a cold plate. Statistical analysis of raw data was performed by analysis of variance (ANOVA), with significance threshold set at $p<0.05$. Analgesic activity was determined as a statistically significant increase in latency time to paw withdrawal in treated animals as compared to vehicle-treated animals. Comparisons for statistically significant differences in latency times were made between PPAR agonist compound-treated animals and vehicle controls, between carbamazepine-treated animals and vehicle controls, and between PPAR agonist compound-treated animals and carbamazepine-treated animals from the same experiment. All statistically significant differences between compared groups are indicated by the brackets, with *=$p<0.05$, and **=$p<0.001$.

Embodiments of the invention provide methods for treating neuropathic pain by the administration of a therapeutically effective amount of an agonist of PPARγ of Formula I or Formula II.

According to embodiments of the invention, a therapeutically effective amount of a compound of Formula I or Formula II that agonizes PPARγ is administered to a subject to treat neuropathic pain. In one embodiment of the invention, the therapeutically effective amount of a compound of Formula I or Formula II that agonizes PPARγ is administered to a subject to treat pain in a subject with postherpetic neuralgia, trigeminal neuralgia, AIDS-related neuropathy, diabetic neuropathy, chronic low back pain, or cancer neuropathy. In another embodiment of the invention, the therapeutically effective amount of a compound of Formula I or Formula II that agonizes PPARγ is administered to a subject to treat pain in a subject with postherpetic neuralgia, trigeminal neuralgia, AIDS-related neuropathy, chronic low back pain, or cancer neuropathy. In another embodiment of the invention, the therapeutically effective amount of a compound of Formula I or Formula II that agonizes PPARγ is administered to a subject to treat neuropathic pain, wherein the subject does not have diabetic neuropathy. A compound useful in carrying out a therapeutic method embodiment of the invention is advantageously formulated in a pharmaceutical composition in combination with a pharmaceutically acceptable carrier. The amount of compound in the pharmaceutical composition depends on the desired dosage and route of administration. In one embodiment, suitable dose ranges of the active ingredient are from about 1 μg/kg to about 100 mg/kg of body weight taken at necessary intervals (e.g., daily, every 12 hours, etc.). In another embodiment, a suitable dosage range of the active ingredient is from about 2 μg/kg to about 200 μg/kg of body weight taken at necessary intervals. In another embodiment, a suitable dosage range of the active ingredient is from about 20 μg/kg to about 125 μg/kg of body weight taken at necessary intervals.

In one embodiment of the method of treating neuropathic pain, the dosage and administration are such that PPARγ is only partially inhibited so as to avoid any unacceptably deleterious effects.

A therapeutically effective compound can be provided to the subject in a standard formulation that includes one or more pharmaceutically acceptable additives, such as excipients, lubricants, diluents, flavorants, colorants, buffers, and disintegrants. The formulation may be produced in unit dosage form for administration by oral, parenteral, transmucosal, intranasal, rectal, vaginal, or transdermal routes. Parenteral routes include intravenous, intra-arterial, intramuscular, intradermal subcutaneous, intraperitoneal, intraventricular, intrathecal, and intracranial administration.

The pharmaceutical composition can be added to a retained physiological fluid such as blood or synovial fluid. In one embodiment, for example, to target the peripheral nervous system (PNS), the pharmaceutical composition has a restricted ability to cross the blood brain barrier and can be administered using techniques known in the art.

In another embodiment of the method of treating neuropathic pain, the agonist of PPARγ is delivered in a vesicle, particularly a liposome. In one embodiment, the agonist of PPARγ is delivered topically (e.g., in a cream) to the site of pain (or related disorder) to avoid the systemic effects of agonizing PPARγ in non-target cells or tissues.

In another embodiment of the method of treating neuropathic pain, the therapeutic agent is delivered in a controlled release manner. For example, a therapeutic agent can be administered using intravenous infusion with a continuous pump, or in a polymer matrix such as poly-lactic/glutamic acid (PLGA), or in a pellet containing a mixture of cholesterol and the active ingredient, or by subcutaneous implantation, or by transdermal patch.

Specific examples of methods of treating neuropathic pain according to the invention include administration of therapeutically effective amounts of a PPARγ agonist of Formula II selected from the group consisting of: 6-benzenesulfonylcarbamoyl-1-(2-chlorobenzyl)-2-methylbenzimidazole, 6-benzenesulfonylcarbamoyl-1-(biphenyl-4-ylmethyl)-2-ethylbenzimidazole, 5-benzenesulfonylcarbamoyl-1-(2-chlorobenzyl)-2-methylbenzimidazole, 5-(4-chlorobenzenesulfonyl-carbamoyl)-1-(2-chlorobenzyl)-2-methylbenzimidazole, 1-(2-chlorobenzyl)-2-methyl-5-(2-naphthalenesulfonylcarbamoyl)-benzimidazole, 1-(2-chlorobenzyl)-6-methanesulfonylcarbamoyl-2-methylbenzimidazole, 6-(1-butanesulfonylcarbamoyl)-1-(2-chlorobenzyl)-2-methylbenzimidazole, 1-(2-chlorobenzyl)-2-methyl-6-(1-octanesulfonylcarbamoyl)benzimidazole, 1-(2-chlorobenzyl)-2-methyl-6-(2-propanesulfonylcarbamoyl)benzimidazole, 1-(biphenyl-4-ylmethyl)-6-(1-butanesulfonylcarbamoyl)-2-methylbenzimidazole, 6-(1-butanesulfonylcarbamoyl)-1-(2,4-dichlorobenzyl)-2-methylbenzimidazole, 1-(biphenyl-4-ylmethyl)-6-(1-butanesulfonylcarbamoyl)-2-ethylbenzimidazole, 6-benzenesulfonylcarbamoyl-1-(biphenyl-4-ylmethyl)-2-trifluoromethylbenzimidazole, 5-benzenesulfonylcarbamoyl-1-(biphenyl-4-ylmethyl)-2-trifluoromethylbenzimidazole, 6-benzenesulfonylcarbamoyl-2-cyclopropyl-1-(2-fluorobenzyl)benzimidazole, Nbenzenesulfonyl-3-[1-(2-chlorobenzyl)-2-methylbenzimidazol-6-yl]acrylamide, N-benzenesulfonyl-2-[1-(2-chlorobenzyl)-2-methylbenzimidazol-6-yl]acetamide, 1-(2-chlorobenzyl)-2-methyl-6-(2-naphthalenesulfonylcarbamoyl)benzimidazole, 1-(2-chlorobenzyl)-2-methyl-6-(1-naphthalenesulfonylcarbamoyl)benzimidazole, 6-(4-chlorobenzenesulfonylcarbamoyl)-1-(2-chlorobenzyl)-2-methylbenzimidazole, 6-(3-chlorobenzenesulfonylcarbamoyl)-1-(2-chlorobenzyl)-2-methylbenzimidazole, 5-benzenesulfonylcarbamoyl-2-benzyl-1-(2-chlorobenzyl)benzimidazole, 6-benzenesulfonylcarbamoyl-2-benzyl-1-(2-chlorobenzyl)benzimidazole, 6-benzenesulfonylcarbamoyl-1-(biphenyl-4-ylmethyl)-2-methylbenzimidazole, 1-(2-chlorobenzyl)-2-methyl-6-trifluoromethanesulfonylcarbamoylbenzimidazole, 6-benzenesulfonylcarbamoyl-1-(2,4-dichlorobenzyl)-2-methylbenzimidazole, 1-(2-chlorobenzyl)-6-(4-methoxybenzenesulfonylcarbamoyl)-2-methylbenzimidazole, 1-(2-chlorobenzyl)-2-methyl-6-α-toluenesulfonylcarbamoyl)benzimidazole, 1-(2-chlorobenzyl)-6-(2,5-dimethylbenzenesulfonylcarbamoyl)-2-methylbenzimidazole, 1-(2-chlorobenzyl)-2-methyl-6-(4-nitrobenzenesulfonylcarbamoyl)-benzimidazole, 1-(2-chlorobenzyl)-2-methyl-6-[4-(trifluoromethyl)benzenesulfonylcarbamoyl]benzimidazole, 6-(2-chlorobenzenesulfonylcarbamoyl)-1-(2-chlorobenzyl)-2-methylbenzimidazole, 6-benzenesulfonylcarbamoyl-2-benzyl-1-(2,4-dichlorobenzyl)benzimidazole, 5-benzenesulfonylcarbamoyl-2-benzyl-1-(2,4-dichlorobenzyl)benzimidazole, 6-benzenesulfonylcarbamoyl-1-(biphenyl-4-ylmethyl)-2-hydroxybenzimidazole, 6-benzenesulfonylcarbamoyl-1-(biphenyl-4-ylmethyl)-2-mercaptobenzimidazole, 6-benzenesulfonylcarbamoyl-1-(biphenyl-4-ylmethyl)-2-methoxybenzimidazole, 6-benzenesulfonylcarbamoyl-1-(biphenyl-4-ylmethyl)-2-carboxybenzimidazole, 6-benzenesulfonylcarbamoyl-1-(biphenyl-4-ylmethyl)-2-methylaminobenzimidazole, 2-amino-6-benzenesulfonylcarbamoyl-1-(biphenyl-4-ylmethyl)-benzimidazole, 6-benzenesulfonylcarbamoyl-1-(biphenyl-4-ylmethyl)-2-n-propylbenzimidazole, 6-benzenesulfonylcarbamoyl-1-(biphenyl-4-ylmethyl)-2-n-heptylbenzimidazole, 6-benzenesulfonylcarbamoyl-1-(biphenyl-4-ylmethyl)-2-chloromethylbenzimidazole, 6-benzenesulfonylcarbamoyl-1-(biphenyl-4-ylmethyl)-2-methoxymethylbenzimidazole, 6-benzenesulfonylcarbamoyl-1-(biphenyl-4-ylmethyl)-2-i-propylbenzimidazole, 6-benzenesulfonylcarbamoyl-1-(biphenyl-4-ylmethyl)-2-methylthiobenzimidazole, 6-benzenesulfonylcarbamoyl-1-(biphenyl-4-ylmethyl)-2-ethylthiobenzimidazole, 6-benzenesulfonylcarbamoyl-1-(biphenyl-4-ylmethyl)-2-npropylthiobenzimidazole, 6-benzenesulfonylcarbamoyl-1-(biphenyl-4-ylmethyl)-2-n-hexylthiobenzimidazole, 6-benzenesulfonylcarbamoyl-1-(biphenyl-4-ylmethyl)benzimidazole, 6-benzenesulfonylcarbamoyl-1-(2,4-difluorobenzyl)-2-methylbenzimidazole, 6-benzenesulfonylcarbamoyl-1-(biphenyl-4-ylmethyl)-2-phenylbenzimidazole, 6-benzenesulfonylcarbamoyl-2-methyl-1-(2-nitrobenzyl)-benzimidazole, 6-benzenesulfonylcarbamoyl-2-methyl-1-benzylbenzimidazole, 6-benzenesulfonylcarbamoyl-2-methyl-1-(4-nitrobenzyl)benzimidazole, 6-benzenesulfonylcarbamoyl-1-(4-benzyloxybenzyl)-2-methylbenzimidazole, 6-benzenesulfonylamino-methyl-1-(2-chlorobenzyl)-2-methylbenzimidazole, N-benzenesulfonyl-3-[1-(2-chlorobenzyl)-2-methylbenzimidazol-6-yl]propionamide, 6-benzenesulfonylcarbamoyl-2-methyl-1-[4-(1,2,3-thiadiazol-4-yl)benzyl]benzimidazole, 1-(2-chlorobenzyl)-2-methyl-6-(8-quinolinesulfonylcarbamoyl)benzimidazole, 6-(4-t-butylbenzenesulfonylcarbamoyl)-1-(2-chlorobenzyl)-2-methylbenzimidazole, 6-benzenesulfonylcarbamoyl-2-methyl-1-[4-(trifluoromethyl)benzyl]benzimidazole, 5-benzenesulfonylcarbamoyl-2-methylbenzimidazole, 1-(biphenyl-4-ylmethyl)-6-(1-butanesulfonylcarbamoyl)-2-methoxymethylbenzimidazole, 1-(4-benzyloxybenzyl)-6-(1-butanesulfonylcarbamoyl)-2-methoxymethylbenzimidazole, 6-(1-butanesulfonylcarbamoyl)-1-(2,4-dichlorobenzyl)-2-methoxymethylbenzimidazole, 1-(2-chlorobenzyl)-2-methyl-6-(1-propanesulfonylcarbamoyl)benzimidazole, 6-ethanesulfonylcarbamoyl-1-(2-chlorobenzyl)-2-methylbenzimidazole, 6-(propanesultam-1-ylcarbonyl)-1-(2-chlorobenzyl)-2-methylbenzimidazole, 6-benzenesulfonylcarbamoyl-1-(biphenyl-4-ylmethyl)-2-cyclopropylbenzimidazole, 1-(2-chlorobenzyl)-2-methyl-6-(1-pentanesulfonylcarbamoyl)benzimidazole, 1-(2-chlorobenzyl)-2-methyl-6-[(3-methylbutane)sulfonylcarbamoyl]-benzimidazole, 1-(2-chlorobenzyl)-6-(1-hexanesulfonylcarbamoyl)-2-methylbenzimidazole, 7-(1-butanesulfonylcarbamoyl)-1-(2,4-dichlorobenzyl)-2-methylbenzimidazole, 1-(2-chlorobenzyl)-2-methyl-6-[1-[3-(trimethylsilyl)propane]sulfonylcarbamoyl]-benzimidazole, 4-(1-butanesulfonylcarbamoyl)-1-(2,4-dichlorobenzyl)-2-methylbenzimidazole, 1-(4-benzyloxybenzyl)-6-(1-butanesulfonylcarbamoyl)-2-methylbenzimidazole, 6-(1-butanesulfonylcarbamoyl)-1-[(2'-cyanobiphenyl-4-yl)methyl]-2-methylbenzimidazole, 6-(1-ethanesulfonylcarbamoyl)-1-[(2'-fluorobiphenyl-4-yl)methyl]-2-methylbenzimidazole, 6-(1-butanesulfonylcarbamoyl)-1-[(3-fluorobiphenyl-4-yl)methyl]-2-methylbenzimidazole, 1-(2-chlorobenzyl)-6-[(2-methoxyethane)-sulfonylcarbamoyl]-2-methylbenzimidazole, 1-(2-chlorobenzyl)-6-(1-hexanesulfonylcarbamoyl)-2-methylbenzimidazole, 1-(2,4-dichlorobenzyl)-2-methyl(1-pentanesulfonylcarbamoyl)-benzimidazole, 1-(biphenyl-4-ylmethyl)-2-ethyl-6-[1-[3-(methylthio)propane]sulfonylcarbamoyl]benzimidazole, 1-(4-biphenylmethyl)-2-ethyl-6-(1-pentanesulfonylcarbamoyl)benzimidazole, 6-(1-butanesulfonylcarbamoyl)-1-(2,4-dichlorobenzyl)-2-ethylbenzimidazole, 1-(4-biphenylmethyl)-2-ethyl-6-[1-(3-methyl)-butanesulfonylcarbamoyl]benzimidazole, 5-(1-butanesulfonylcarbamoyl)-1-(2,4-dichlorobenzyl)-2-methylbenzimidazole, 1-(4-biphenylmethyl)-5-(1-butanesulfonylcarbamoyl)-2-ethylbenzimidazole, 1-(4-biphenylmethyl)-2-ethyl-6-(2-methoxyethanesulfonylcarbamoyl)benzimidazole, 6-(1-butanesulfonylcarbamoyl)-2-ethyl-1-[4-(4-fluorobenzyloxy)benzyl]benzimidazole, 6-(1-butanesulfonylcarbamoyl)-1-[4-(3,4-dichlorobenzyloxy)-benzyl]-2-ethylbenzimidazole, 6-(1-butanesulfonylcarbamoyl)-1-[sec-(2,4-dichlorophenethyl)]-2-methylbenzimidazole, 6-(1-butanesulfonylcarbamoyl)-1-[4-(2-pyridyl)benzyl]-2-methylbenzimidazole, 6-(1-butanesulfonylcarbamoyl)-1-(2,4-dichlorobenzyl)-2,4-dimethylbenzimidazole, 6-(1-butanesulfonylcarbamoyl)-2-methyl-1-(4-phenoxybenzyl)benzimidazole, 6-(butanesulfonylcarbamoyl)-2-methyl-1-(2-pyridylmethyl) benzimidazole, 1-[(4-benzoylamino)benzyl]-6-(1-butanesulfonylcarbamoyl)-2-methylbenzimidazole, 6-(1-butanesulfonylcarbamoyl)-2-methyl-[4-(2-phenylethyl)benzyl] benzimidazole, 1-[(4-benzoyl)benzyl]-6-(1-butanesulfonylcarbamoyl)-2-methylbenzimidazole, 6-(1-butanesulfonylcarbamoyl)-2-methyl-[4-(2-phenylethenyl) benzyl]-benzimidazole, 1-(dibenzofuran-2-ylmethyl)-6-(1-butanesulfonylcarbamoyl)-2-methylbenzimidazole, 6-(1-butanesulfonylcarbamoyl)-1-(2,4-dichlorobenzyl)-2-hydroxybenzimidazole, 6-(1-butanesulfonylcarbamoyl)-2-methyl-1-(2-quinolylmethyl)benzimidazole, and 6-(1-butanesulfonylcarbamoyl)-2-methyl-1-[3-(4-bromoisoquinolyl)methyl]benzimidazole.

Experimental Protocol

Three neuropathic pain models in rats have been shown to correlate well to clinical outcome both with respect to the rank order of active (Gabapentin, Pregabalin, Amitriptyline, Carbamazepine and N-type Ca++ blockers) and inactive (SSRI and NSAIDs) substances, and also between experimental and effective therapeutic doses. These models are based on three surgical procedures: (i) the spinal nerve ligation (SNL) [Kim, S, and J. Chung, An experimental model for peripheral neuropathy produced by segmental spinal nerve ligation in the rat. Pain, 1992. 50: p. 355-363]; (ii) the partial sciatic nerve lesion (Seltzer) [Seltzer, Z., R. Dubner, and Y. Shir, A novel behavioral model of neuropathic pain disorders produced in rats by partial sciatic nerve injury. Pain, 1990. 43: p. 205-218]; (iii) and the chronic constriction injury [Bennett, G. and Y. Xie, A peripheral mononeuropathy in rat that produces disorders of pain sensation like those seen in man. Pain, 1988. 33: p. 87-107]. The Bennett model was used, as described below.

Animals:

Young adult, male Sprague Dawley rats (200-250 g) from Harlan were used. Upon receipt, animals were assigned unique identification numbers (tail marked) and housed 2-3 per cage in suspended polycarbonate rat cages with filter paper covering mesh shelf. Rats were acclimated for up to 7 days prior to surgery. During the period of acclimation, rats were examined on a regular basis, handled, and weighed to assure adequate health and suitability. Animals were maintained on a 12/12 light/dark cycle. The room temperature was maintained between 20 and 23 C with a relative humidity maintained between 30% and 70%. Chow and water were provided ad libitum for the duration of the study. In each test, animals were randomly assigned across treatment groups. Each treatment group contained at least ten animals. All animals were euthanized after the completion of the study.

Drugs:

All compounds were suspended in 5% Tween80, 5% PEG in saline and administered orally at a dose volume of 1 ml/kg. In all experiments carbamazepine, per oral, was used as a positive control.

Apparatus:

The apparatus consists of a cold plate (Ugo Basile Hot/Cold Plate) measuring 25 (w)×37 (d)×16 (h) cm with a 10 cm thick aluminum circular plate. Additionally, a clear Plexiglas cylinder measuring 20 (d)×25 (h) cm is placed on top of the plate. Neuropathic rats (7-8 days after surgical sciatic nerve ligation) were habituated to the testing room for at least 1 hr. Baseline responses were measured on the day prior to drug administration. Each animal was tested by placing it on the cold plate (set to 4 C) and the latency of paw withdrawal was recorded.

Surgery:

Chronic constrictive nerve injury of the sciatic nerve was performed according to Bennett and Xie (1988). Specifically, rats were anesthetized with isoflurane (2% in air). The left hind flank was shaved and sterilized and the rat positioned on its side. The pelvic bone ridge was palpated and a vertical incision was made perpendicular to the long axis of the spine. The first layer of muscle was cut to expose the sciatic nerve. Retractors were used to open incision, centering the portion of the sciatic nerve to be ligated. The exposed nerve was carefully teased apart from the second layer of muscle, removing fascia lining. Once the nerve was freed, hooked forceps were carefully passed underneath the nerve in order to pass 5 cm lengths of 4.0 chromic gut suture under the nerve (sutures were pre-soaked in saline to ensure softness). Sutures were positioned superior to the point where the nerve branches. Each length of suture was used to make a loose ligation around the nerve (only tight enough to elicit a twitch). All sutures were within a 0.5 cm range of each other. The incision was closed in layers, using 4.0 silk sutures, and the skin was closed using sterile autoclips. Topical antibiotic ointment was applied to the sutured incision. All subjects received buprenorphine (0.05 mg/kg in a volume of 1 ml/kg, i.p.) immediately before and after surgery. Each subject was monitored until it was awake and moving freely around the recovery chamber. Animals were then single-housed for the duration of the study.

Experimental Results

Figure 2:
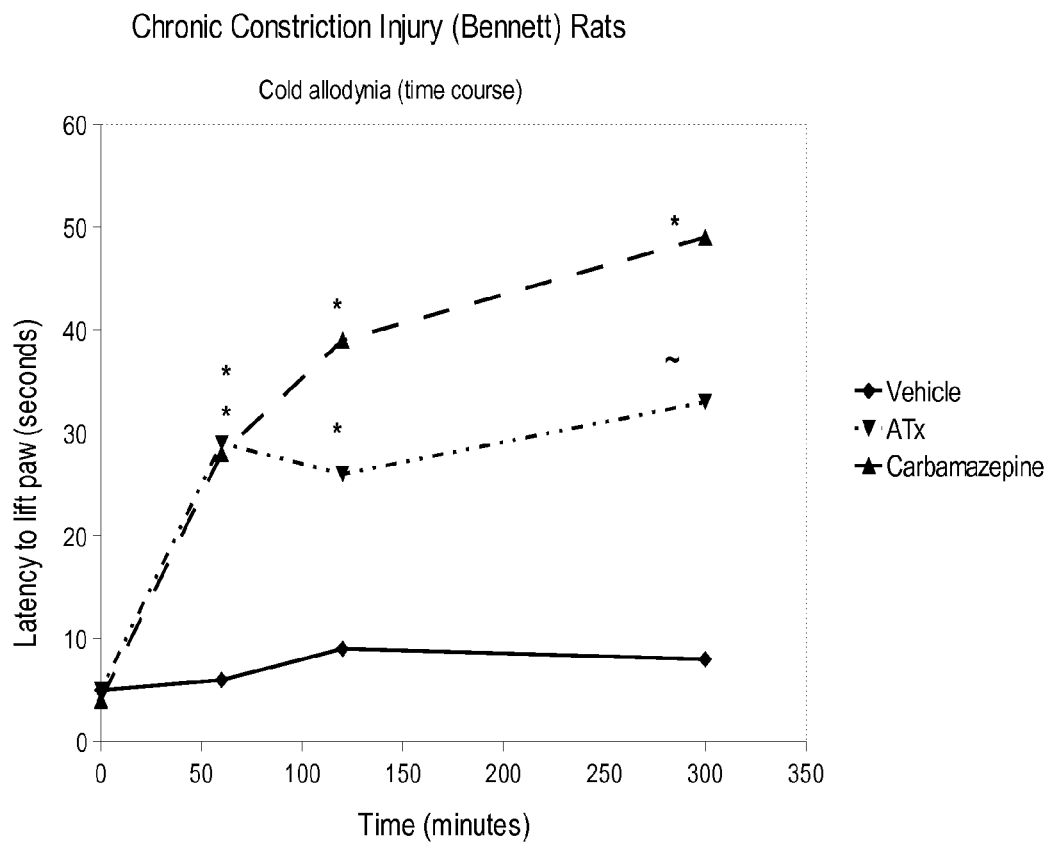
FIG. 2—Effect of carbamazepine (+ control) and 3-(2,4-dichlorobenzyl)-2-methyl-N-(pentylsulfonyl)-3H-benzimidazole-5-carboxamide ("Atx" in Figure) on the latency to lift paw from the cold plate at different time points following administration of 100 mg/kg PO in the Bennett model. Statistical analysis of data as for FIG. 1; *=p, 0.05 and ~=$p<0.1$ compared to vehicle control.
Figure 3:
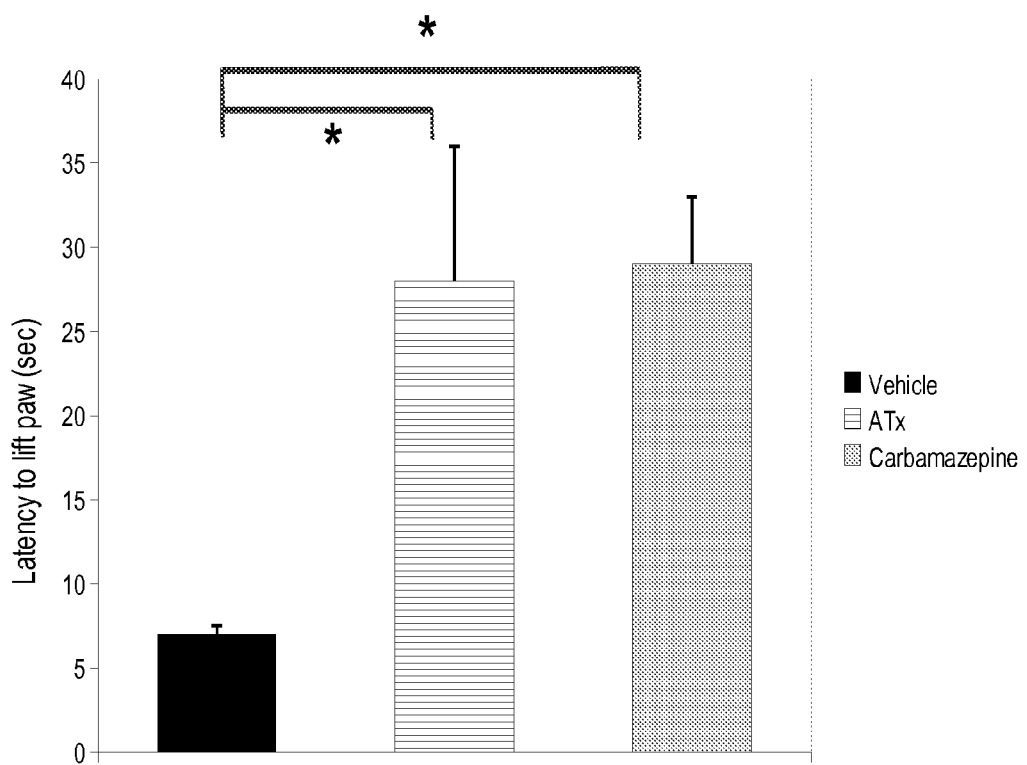
FIG. 3—Effect of carbamazepine (+ control) and 3-(2,4-dichlorobenzyl)-2-methyl-N-(pentylsulfonyl)-3H-benzimidazole-5-carboxamide ("Atx" in Figure) on the latency to lift paw from the cold plate 60 min following compound injection, in rats with the Bennett model of neuropathic pain. Data represent mean±SEM. Statistical analysis of data as for FIG. 1; *=$p<0.05$. Note that ATx-treated animals show analgesic activity which is significantly greater than vehicle alone, and not significantly different from carbamazepine.
Figure 4:
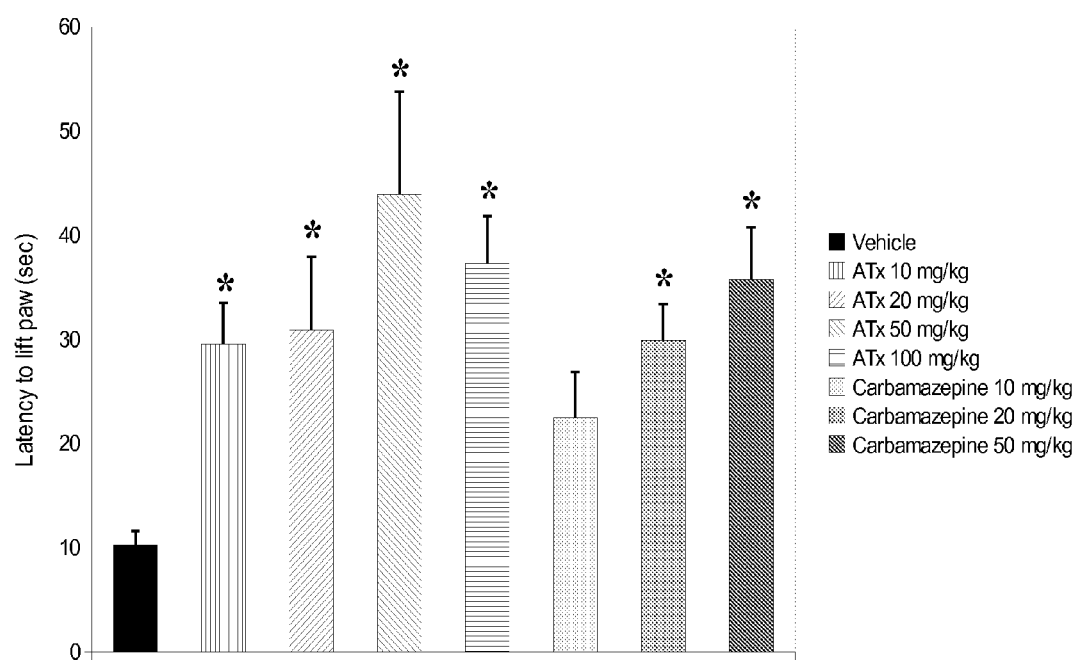
FIG. 4—Dose response of 3-(2,4-dichlorobenzyl)-2-methyl-N-(pentylsulfonyl)-3H-benzimidazole-5-carboxamide ("Atx" in Figure) and carbamazepine (+ control) on the latency to lift paw from the cold plate in rats with the Bennett neuropathic pain model. Paw latency times were measured at 1 hour following administration of compounds at different doses PO. Statistical analysis of data as for FIG. 1; *=$p<0.05$.

Experimental results for a representative compound of Formula I and Formula II, 3-(2,4-dichlorobenzyl)-2-methyl-N-(pentylsulfonyl)-3H-benzimidazole-5-carboxamide, are shown in FIGS. 1-4.

All chemical groups recited herein are defined according to the disclosure of Yamasaki et al. in EP 0882718 B1.

Any of the compounds described herein can be administered as a prodrug to increase the activity, bioavailability, stability or otherwise alter the properties of the selected compound. A number of prodrug ligands are known.

The term "medicament" means a substance used in a method of treatment and/or prophylaxis of a subject in need thereof, wherein the substance includes, but is not limited to, a composition, a formulation, a dosage from, and the like, comprising a compound of Formula I or Formula II. It is contemplated that the use of a compound of a method of the invention in the manufacture of a medicament for the treatment of any of the conditions disclosed herein can be any of the compounds contemplated in any of the aspects of the invention, either alone or in combination with other compounds of the methods of the present invention.

The term "therapeutically effective amount" as used herein means an amount required to reduce symptoms of neuropathic pain in an individual. The dose will be adjusted to the individual requirements in each particular case. That dosage can vary within wide limits depending upon numerous factors such as the severity of the condition to be treated, the age and general health condition of the patient, other medicaments with which the patient is being treated, the route and form of administration and the preferences and experience of the medical practitioner involved. For oral administration, a daily or twice daily dosage of between about 0.1 and about 10 mg, including all values in between, such as 0.25, 0.5, 0.75, 1, 1.5, 2, 2.5, 3, 3.5, 4, 4.5, 5, 5.5, 6, 6.5, 7, 7.5, 8, 8.5, 9, and 9.5, per day should be appropriate in monotherapy and/or in combination therapy. One twice daily dosage embodiment is between about 0.5 and about 7.5 mg twice per day. Another twice daily dosage embodiment is between 1.0 and about 6.0 mg twice per day. One of ordinary skill in treating conditions described herein will be able, without undue experimentation and in reliance on personal knowledge, experience, and the disclosures of this application, to ascertain a therapeutically effective amount of the compounds of the methods of the present invention for a given condition and patient.

We claim:

1. A method of treating pain associated with postherpetic neuralgia, comprising administering a pharmaceutical composition to a mammal in need of such treatment, wherein the pharmaceutical composition comprises a therapeutically effective amount of an agonist of PPARγ which is a compound of formula II:

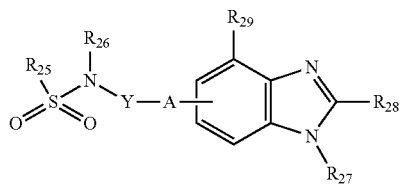

wherein
- R27 represents an aryl lower alkyl group whose aryl moiety may be substituted by one or two substituents selected from a halogen atom or an aryl group;
- R28 represents a lower alkyl group or a lower cycloalkyl group;
- R29 represents a hydrogen atom or a lower alkyl group;
- R25 represents an alkyl group having up to 8 carbon atoms or an aryl group;
- Y represents a carbonyl group; and
- A represents a single bond;

or a pharmaceutically acceptable salt thereof.

2. The method of treating pain of claim 1, wherein the mammal is a human.

3. The method of treating pain of claim 2, wherein the agonist of PPARγ is 3-(2,4-dichlorobenzyl)-2-methyl-N-(pentylsulfonyl)-3H-benzimidazole-5-carboxamide or a pharmaceutically acceptable salt thereof.

* * * * *